United States Patent [19]
Terwilliger

[11] Patent Number: 5,766,135
[45] Date of Patent: Jun. 16, 1998

[54] ECHOGENIC NEEDLE TIP

[76] Inventor: Richard A. Terwilliger, 3321 Rockwood La. South, Estes Park, Colo. 80517

[21] Appl. No.: 731,688

[22] Filed: Oct. 17, 1996

Related U.S. Application Data

[63] Continuation of Ser. No. 400,368, Mar. 8, 1995, abandoned.

[51] Int. Cl.$^6$ ........................................... A61B 5/00
[52] U.S. Cl. ................................. 600/567; 600/562
[58] Field of Search .................. 128/662.05, 749, 128/751–754

[56] References Cited

U.S. PATENT DOCUMENTS

| | | | |
|---|---|---|---|
| 4,401,124 | 8/1983 | Guess et al. | 128/660 |
| 5,048,530 | 9/1991 | Hurwitz | 128/662.05 |
| 5,081,997 | 1/1992 | Bosley, Jr. et al. | 128/662.02 |
| 5,161,542 | 11/1992 | Palestrant | 128/754 |
| 5,201,314 | 4/1993 | Bosley et al. | 128/662.02 |

OTHER PUBLICATIONS

"SonoVu US–A visible improvement in ultrasound–guided aspiration"; 1–page; ©1990.

*Primary Examiner*—Max Hindenburg
*Attorney, Agent, or Firm*—Fliesler, Dubb, Meyer & Lovejoy

[57] ABSTRACT

An echogenic needle includes a hole provided at the distal tip end. Preferably the hole is positioned through a centerline which is spaced from the centerline of the stylet in order to form a concave surface from which sound waves are reflected in order to locate the distal tip end.

22 Claims, 2 Drawing Sheets

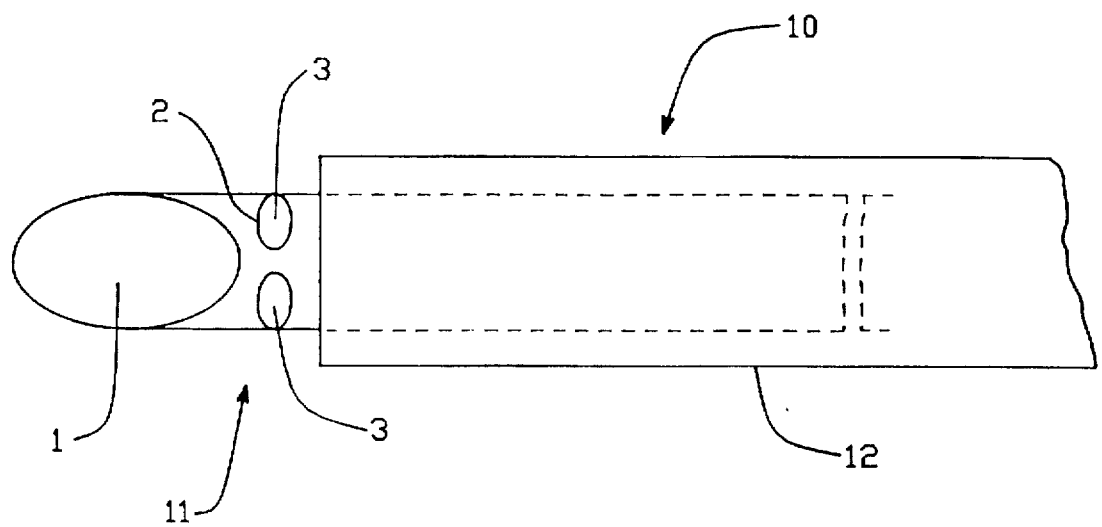
FIG.—1
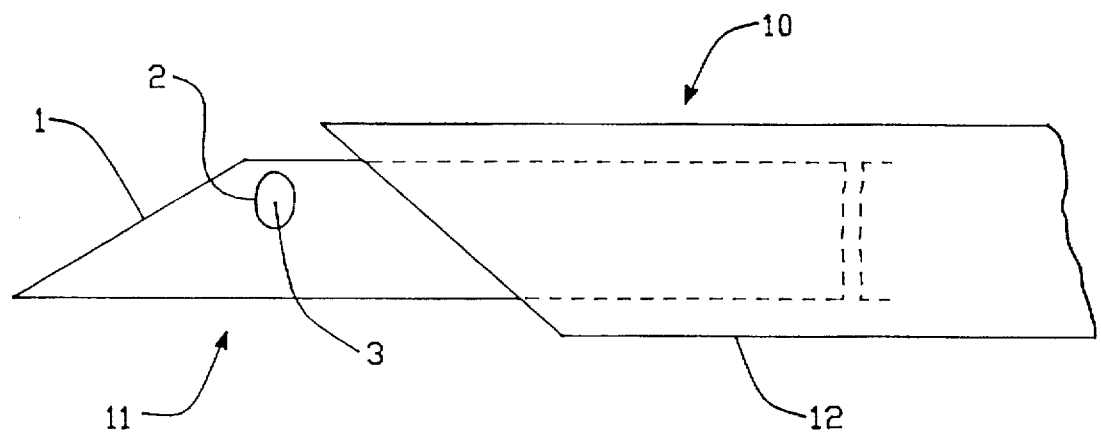
FIG.—2
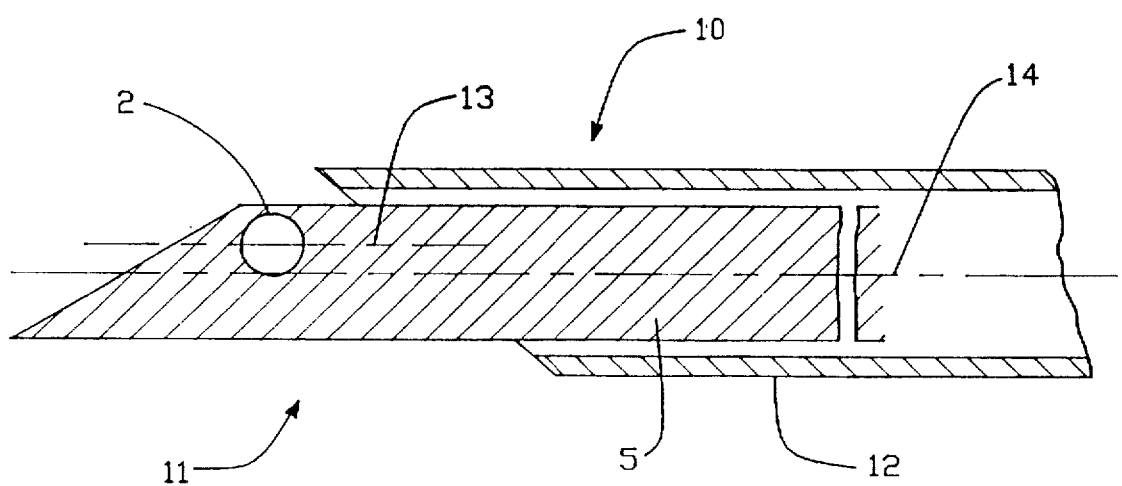
FIG.—3

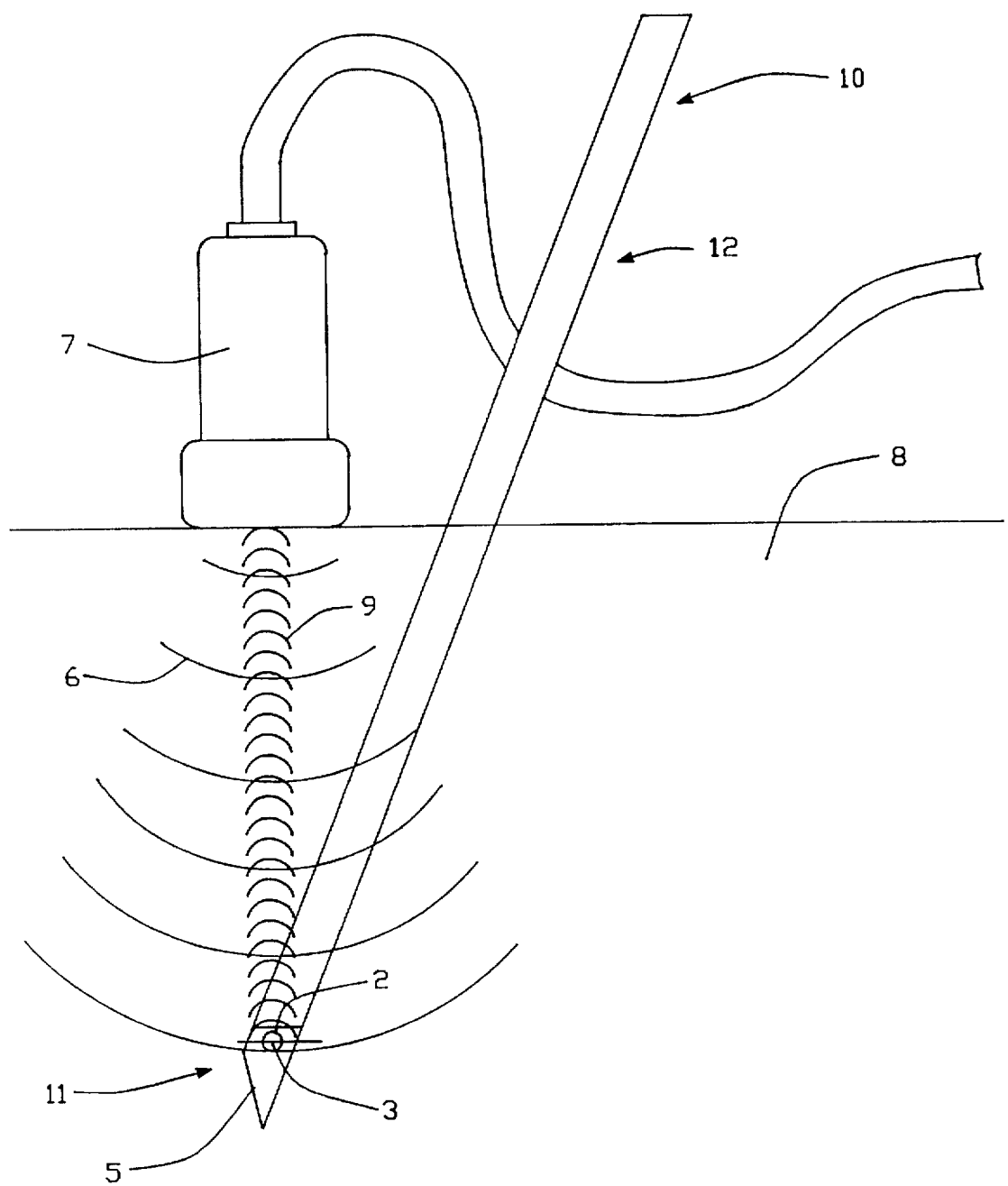
FIG.—4

ECHOGENIC NEEDLE TIP

This application is a continuation of Ser. No. 08/400,368, filed Mar. 8, 1995, now abandoned.

BACKGROUND

1. Field of the Invention

This invention relates to a new needle tip design to enhance the visibility of, and ability to locate the needle tip during an ultrasound guided needle biopsy procedure. The functionality of this needle tip design is independent of the angle of entry of the needle into the tissue, as it relates to the sound waves generated by the ultrasound transceiver.

This improved needle tip design can be used on the needles of either manual or automated biopsy needle instruments used for the performance of tissue extraction from a tissue mass visualized under ultrasound guidance.

2. Background of the Invention

It is often desirable and frequently absolutely necessary to sample or test a portion of tissue from humans and even animals to aid in the diagnosis and treatment of patients with cancerous tumors, premalignant conditions and other diseases or disorders. Typically in the case of cancer or the suspicion of malignant tumors, a very important process call tissue biopsy is performed to establish whether cells are cancerous.

Biopsy may be done by an open or closed technique. Open biopsy removes the entire tissue mass or a part of the tissue mass. Closed biopsy on the other hand is usually performed with a needle-like instrument and may be either an aspiration (hollow needle on a syringe) or a core biopsy (special tissue cutting needle design). In needle aspiration biopsy, individual cells or clusters of cells are obtained for cytologic examination. In core biopsy, a segment of tissue is obtained for histologic examination which may be done as a frozen section or paraffin section.

The methods and procedures of obtaining tissue samples for cytologic or histologic examination have been performed historically by manual insertion and manipulation of the needle. These procedures are performed "blind" by the physician and guided by "feel" and known anatomic "landmarks".

Tumors are first noted in a patient by one of three ways, palpation, X-ray imaging or Ultrasound imaging. Once a tumor is identified, a biopsy procedure is performed. Modern medical opinion dictates early detection of cancer increases the likelihood of successful treatment.

The introduction of ultrasound imaging in the field of medical technology has greatly influenced the field of percutaneous tissue biopsy in the last fifteen years. The use of tissue imaging devices that utilize ultrasound waves allows the physician to "see" inside the body and visually guide the needle to the tumor mass. The inherent problem in visualizing the needle is that the angle of entry of the needle into the body in relationship to the direction of the generation of ultrasound waves precludes an optimized reflection of the ultrasound waves back to the transceiver, thus making it extremely difficult to see the needle in the ultrasound image and locate the needle tip in the image in relationship to the anatomic structures of the body.

Attempts in prior art to solve this problem have relied on surface treatments to the outer surface of the hollow needle tube and have been inadequate or only slightly improved visualization at shallow angles of entry of the needle. Examples of such treatments have been described in U.S. Pat. Nos. 4,401,124 (Guess et al.), 5,081,997 (Bosley et al.), and 5,201,314 (Bosley et al.).

These design limitations create a situation of compromise between the steep angle of entry of the needle that is desired in most procedures and the ability of the needle shaft to reflect the ultrasound waves back to the transceiver, thus allowing the needle to be seen in the ultrasound image.

The prior art surface treatments have been applied to the last part of the distal end of the hollow cannula which is positioned well back from the actual tip of the needle set as it is introduced into the body. This treatment only allows an approximation to be made of the location of the most distal tip of the needle set. The current prior art requires the physician to estimate where the true tip of the needle lies in relation to the internal structures of the tissue.

In order for a surface treatment to be effective at steeper angles of entry, the disrupted surface irregularities must be large enough, in relationship to the length of the sound wave, at the frequencies used to image. If the irregularities are made large enough to properly reflect, the needle shaft is so roughened as to impede the smooth movement of the needle through the tissue and thereby compromising the structure of the tissue to be collected by the needle.

The requirements to be able to visualize the needle tip at all angles of entry and the need to maintain the structure of the tissue to be collected, dictate the need for an alternative approach in a design of the needle tip to allow adequate visualization of the location of the extreme needle tip during ultrasound imaging. The ideal product would allow the needle to smoothly pass though the tissue and still be visualized at any angle of entry, allowing the physician to obtain the necessary tissue required to make a diagnosis.

Accordingly it is a principle object of this invention to provide an improved needle tip design to more reliably visualize the tip of the needle under ultrasound guided biopsy procedures.

It is a further object of this invention to provide a needle tip design that allows the visualization of the needle tip at any angle of entry into the body in relationship to the generation of sound waves by the ultrasound transceiver.

It is a further object of this invention to provide a needle tip design that allows visualization that does not impede the smooth passage of the needle through the surrounding tissue.

It is a further object of this invention to provide an improved needle tip design that allows visualization of the distal tip of the inner stylet, thus allowing the physician to visualize the extreme distal end of the needle set.

These and other objects of the invention will be apparent from the following descriptions and claims.

SUMMARY OF THE INVENTION

Based on the limitations of prior art instruments for enhancing the visibility of the needle tip under ultrasound imaging, there exists a need for a needle tip design which is capable of being visualized at any angle of entry to assist in obtaining biopsy samples with currently available marketed devices.

Accordingly I have invented a needle tip design that overcomes the limitations of prior art devices.

The needle tip design can be made an integral part of the inner solid stylet of any given dual needle set. Typically the needle set consists of an outer hollow cannula and an inner solid stylet. The stylet is used during the introduction of the needle set into the tissue to prevent material from entering the hollow outer needle until the biopsy site is reached.

In a preferred form, the stylet has a hole machined through the distal tip of the diameter of the stylet body, perpendicular to the axis of the stylet. This hole is positioned slightly above the centerline of the stylet so the hole breaks out on the diameter as oval openings.

Due to these oval openings, the bottom curved portion of the hole breakouts presents a reflective concave surface that always presents itself as a surface to reflect back the sound wave emitted from the ultrasound transceiver at any relational angle of the needle shaft to the generation of the sound waves.

Since the hole is small in relationship to the diameter of the stylet body and perpendicular to the axis of the stylet, the movement of the stylet through the tissue is not impeded in any significant way.

BRIEF DESCRIPTION OF THE DRAWINGS

The above noted advantages and other characteristic features of the present invention will be apparent from the accompanying drawings, and in part points out in the following detailed description of the preferred embodiment of the invention in which references will be made to the accompanying drawings wherein like reference numerals designate corresponding parts and wherein:

FIGS. 1 and 2 are top and side views, respectively, of the distal end of the preferred embodiment inventive needle tip design on a stylet as part of a needle set.

FIG. 3 is a cross-sectional view of the preferred embodiment inventive needle tip design showing a cross sectional plane perpendicular to the longitudinal axis of the stylet as part of a needle set.

FIG. 4 is a perspective view of the preferred embodiment of a needle set with the needle tip design as part of a stylet. This is a representative depiction of the sound waves interacting with the needle tip design.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless understood that no limitation of the scope of the invention is thereby intended, such alterations and further modifications in the illustrated device, and such further applications of the principles of the invention as illustrated therein being contemplated as would normally occur to one skilled in the art to which the invention relates.

Considering now the drawings in detail:

FIGS. 1 and 2 show the top and side view of the distal end of the inventive needle tip design. The needle set 10 is comprised in this embodiment of a stylet 11 and a cannula 12. Note that in FIG. 1, the needle or stylet tip 1 shows the side regions of the stylet 11 where the perpendicular hole 2 breaks out on both sides of the stylet diameter. This region where the hole 2 breaks out allows the concave bottom surface 3 to present itself to the generated sound waves and bounce them back to the transceiver.

FIG. 3 illustrates the position of the centerline 13 of the perpendicular hole 2 in relation to the centerline 14 of the stylet body 5. It is noted that the centerline 13 of the hole 2 is slightly above the centerline 14 of the stylet. The centerline 13 may be even more removed from the centerline 14 as long as sufficient concave bottom surface 3 remains for good ultrasound imaging. In this embodiment as shown in FIG. 3, the diametrical centerline 13 is substantially parallel to the longitudinal centerline 14.

FIG. 4 pictorially illustrates the ability of the transmit sound waves 6 generated from the transceiver 7 to reflect off the exposed concave surfaces 3 of the perpendicularly drilled hole 2 in the stylet body 5 while positioned in the tissue 8. The return echo 9, reflects back from the exposed concave surface 3 to the transceiver 7, creating a bright indication in the ultrasound image.

By way of example only, the present invention can be used in biopsy devices disclosed in the following U.S. patents and U.S. patent applications, all of which are incorporated herein. The U.S. patents include U.S. Pat. Nos. 5,183,052, 5,188,118 and 5,282,476. The U.S. patent applications include Ser. Nos. 08/218,261 and 08/227,660.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. Thus, by way of example, only the stylet could be used without a cannula in order to locate a surgical site and verify that location with ultrasound imaging. Further, the inventive needle tip could be used on a device other than a stylet and have the present ultrasound imaging advantages.

I claim:

1. A stylet for positioning adjacent to tissue to be biopsed comprising:

a stylet body with an outer surface;

a stylet tip located at a distal end of the stylet body for positioning adjacent to tissue to be biopsed;

an indentation defined at the stylet tip in order to make the stylet echogenic;

said stylet body has a longitudinal centerline; and said indentation pierces said outer surface of said stylet body and said indentation is directed into said stylet body away from said outer surface, and along an axis that does not intersect the longitudinal centerline, in order not to impede the movement of the stylet through tissue to be biopsed.

2. The stylet of claim 1 wherein:

said indentation is concave.

3. The stylet of claim 1 wherein:

said indentation is made by creating at least one hole at the end of the stylet tip.

4. The stylet of claim 1 wherein:

rearwardly of the indentations, the stylet body is smooth in order to provide for smooth passage of the stylet body through tissue.

5. The stylet of claim 1 wherein:

said indentation is elliptical.

6. A stylet for positioning adjacent to tissue to be biopsed comprising:

a solid stylet body;

a stylet tip located at a distal end of the stylet body for positioning adjacent to tissue to be biopsed; and a hole provided in the stylet body adjacent to the stylet tip in order to make the stylet echogenic.

7. The stylet of claim 6 wherein:

said solid stylet body has a first longitudinal centerline; and said hole is provided on a second centerline which is spaced from the first longitudinal centerline.

8. The stylet of claim 6 wherein:

said hole pierces an outer surface of the solid stylet body in order to define a concave shape.

9. The stylet of claim 8 wherein:

said hole is elliptical.

10. The stylet of claim 6 wherein:

rearwardly of the indentation, the stylet body is smooth in order to provide for smooth passage of the stylet body through tissue.

11. A needle set comprising:

a stylet having a stylet body;

a stylet tip located at a distal end of the stylet body adapted for positioning adjacent to tissue to be biopsed;

an echogenic mark defined at the stylet tip in order to make the stylet tip echogenic;

a cannula with an inner bore which receives the stylet body; and said stylet positioned in the cannula body preparatory to the needle set addressing tissue to be biopsed with the stylet tip and echogenic mark positioned just past and outwardly of the tip of the cannula such that the cannula presents a smooth surface for penetrating the tissue while the echogenic mark allows the tip of the stylet to be tracked.

12. The needle set of claim 11 wherein:

said echogenic mark is an indentation.

13. The needle set of claim 11 wherein:

said echogenic mark is a concave indentation.

14. The needle set of claim 11 wherein:

said stylet body has a first longitudinal centerline; and said echogenic mark is provided on a second centerline which is spaced from the first longitudinal centerline.

15. The needle set of claim 11 wherein:

said stylet body has a first longitudinal centerline; and said first longitudinal centerline being included in a plane;

said echogenic mark is provided on a second centerline, which said centerline is spaced from (1) the first longitudinal centerline and (2) the plane.

16. The needle set of claim 11 wherein:

said stylet body has a longitudinal centerline; and said echogenic mark includes first and second side-by-side and spaced apart indentations, which first and second indentations in said side-by-side configuration are substantially perpendicular to said longitudinal centerline.

17. The needle of claim 11 wherein:

said echogenic mark is elliptical.

18. A stylet for positioning adjacent to tissue to be biopsed comprising:

a stylet body;

a stylet tip located at a distal end of the stylet body for positioning adjacent to tissue to be biopsed;

an indentation defined at the stylet tip in order to make the stylet echogenic;

said stylet body has a longitudinal centerline;

said indentation is provided in a direction that does not intersect the longitudinal centerline;

said indentation is made by creating first and second holes at the end of the stylet tip; and wherein said first and second holes pierce through the stylet tip at two adjacent locations in order to define exposed adjacent concave surfaces.

19. A stylet for positioning adjacent to tissue to be biopsed comprising:

a stylet body;

a stylet tip located at a distal end of the stylet body for positioning adjacent to tissue to be biopsed;

an indentation defined at the stylet tip in order to make the stylet echogenic;

said stylet body has a longitudinal centerline;

said indentation is provided in a direction that does not intersect the longitudinal centerline;

said indentation is made by creating first and second holes at the end of the stylet tip; and wherein said first and second holes pierce through the stylet tip at two adjacent locations in order to define side-by-side concave surfaces which concave surfaces in said side-by-side configuration are substantially perpendicular to a longitudinal centerline of said stylet body.

20. A stylet for positioning adjacent to tissue to be biopsed comprising:

a stylet body with an outer surface;

a stylet tip located at a distal end of the stylet body adapted for positioning adjacent to tissue to be biopsed;

an echogenic mark defined at the stylet tip in order to make the stylet tip echogenic;

said stylet body has a longitudinal centerline; and said echogenic mark pierces said outer surface of said stylet body and said echogenic mark is directed into said stylet body away from said outer surface, and along an axis that does not intersect the longitudinal centerline, in order not to impede the movement of the stylet through tissue to be biopsed.

21. A stylet for positioning adjacent to tissue to be biopsed comprising:

a stylet body with an outer surface;

a stylet tip located at a distal end of the stylet body for positioning adjacent to tissue to be biopsed;

an echogenic mark defined at the stylet tip in order to make the stylet tip echogenic;

said echogenic mark includes first and second side-by-side indentations, which side-by-side indentations pierce said outer surface of said stylet body and said indentations are directed into said stylet body away from said outer surface, and along an axis that does not intersect the longitudinal centerline, in order not to impede the movement of the stylet through the tissue to be biopsed.

22. A stylet for positioning adjacent to tissue to be biopsed comprising:

a stylet body with an outer surface;

a stylet tip located at a distal end of the stylet body for positioning adjacent to tissue to be biopsed;

an indentation defined at the style tip in order to make the stylet echogenic;

said stylet body has a longitudinal centerline;

said indentation pierces said outer surface of said stylet body and said indentation is directed into said stylet body away from said outer surface, and along an axis that does not intersect the longitudinal centerline; and said stylet body is solid.

* * * * *